United States Patent [19]

Estes et al.

[11] Patent Number: 5,559,014
[45] Date of Patent: Sep. 24, 1996

[54] METHODS AND REAGENTS TO DETECT AND CHARACTERIZE NORWALK AND RELATED VIRUSES

[75] Inventors: Mary K. Estes, Friendswood; Xi Jiang; David Y. Graham, both of Houston, all of Tex.

[73] Assignee: Baylor College of Medicine, Houston, Tex.

[21] Appl. No.: 485,576

[22] Filed: Jun. 7, 1995

Related U.S. Application Data

[63] Continuation of Ser. No. 433,492, Nov. 8, 1989, abandoned.
[51] Int. Cl.$^6$ ............................ C12N 15/10; C12N 15/40; C12P 19/34
[52] U.S. Cl. .................. 435/91.2; 435/172.3; 435/235.1; 435/5; 536/23.72
[58] Field of Search .................... 435/91.2, 91.33, 435/91.4, 91.51, 91.52, 172.3, 235.1; 935/5, 18, 3, 6; 536/23.72

[56] References Cited

PUBLICATIONS

Cubitt, W. D. et al. 1987. J. Infect. Diseases vol. 156, pp. 806–814.
Black, D. N. et al. 1978. Nature vol. 274, pp. 614–615.
Noonan, K. E. et al. 1988. Nucleic Acids Res. vol. 16, p. 10366.
Greenberg, H. et al. 1981. J. Virol., vol. 37, pp. 994–999.
Jiang, X. et al. 1987. Appl. Envir. Microbiol. vol. 53, pp. 2487–2495.
Kapikian, A. Z. et al. Virology, second edition, edited B. N. Fields et al, Raven Press Ltd, New York. pp. 671–693.
Dingle, J. H. et al. 1953. Am. J. Hyg., vol. 58 pp. 16–30.
Dolin, R. et al. 1972. Proc. Soc. Exp. Med & Biol., vol. 140, pp. 578–583.
Dolin, R. et al. 1971. J. Infect. Dis. vol 123 pp. 307–312.
Dupont, H. L. 1986. New Eng. J. Med. vol 314 pp. 707–708.
Eastaugh, J. et al. 1989. Arch Intern. Med. vol 149 pp. 1735–1740.
Gill, O. N. et al. 1983. Br. Med. J. vol. 287 pp. 1532–1534.
Gunn, R. A. et al. 1982. Am.J.Epidemiol. vol. 115 pp. 348–351.
Jiang, X. et al. 1989. J. Clin. Microbiol. vol. 27 pp. 874–879.
Jiang, X. et al. 1986. Appl. Envir. Microbiol. vol. 52 pp. 711–717.
Kapikian, A. S. et al. 1972. J. Virol. vol. 10 pp. 1075–1081.
Kaplan, J. et al. /1982. Ann. Internal Med. vol 96 pp. 756–761.
Morse, D. L. et al. 1986. New Eng. J. Med. vol. 314 pp. 678–681.
Murphy, A. N. et al. 1979. Med. J. Aust. vol. 2 pp. 329–333.
Sekine, S. et al. 1989. Microbiol Immunol. vol. 33 pp. 207–217.
Thornhill, T. S. et al. 1975. J. Infect. Dis. voll 132 pp. 28–34.
Wilson, R et al. 1982. Am. J. Pub. Health vol. 72 pp. 72–74.
Hayashi, Y. et al. 1989. J. Clin. Microbiol. vol. 27 pp. 1728–1733.
E. O. Caul & Appleton, J. Medical Virology, 1982, 9:257–265.
H. Appleton, Novel Diarrhoea Viruses, Ciba Foundation Symposium 128, 1987, John Wiley & Sons, NY, pp. 108–125.
A. Murphy and D. W. Kingsbury, Fundamental Virology, 2d ed., edited B. N. Fields et al, Raven Press, Ltd., NY, pp. 9–35.

*Primary Examiner*—Mary E. Mosher
*Attorney, Agent, or Firm*—Fulbright & Jaworski L.L.P.

[57] ABSTRACT

Double-stranded cDNA was synthesized from nucleic acid extracted from Norwalk virus purified from stool specimens of volunteers. One clone was isolated from a cDNA library constructed in a pUC-13 vector after amplification of the cDNA. The specificity of this cDNA (pACNV-953) was shown by hybridization assays. The cDNA reacted with post- (but not pre-) infection stool samples from Norwalk volunteers and with highly purified Norwalk virus, but not with other common enteric viruses such as hepatitis A virus and rotavirus. Finally, the probe detected virus in the same fractions of CsCl gradients in which viral antigen was detected using a specific Norwalk virus radioimmunoassay, and particles were detected by immune electron microscopy. Single-stranded RNA probes derived from the DNA clone after subcloning into an in vitro transcription vector were also used to show that the Norwalk virus contains a ssRNA genome of about 8 kb in size. The availability of a Norwalk-specific cDNA and the first partial genome sequence information allow rapid cloning of the entire genome and of establishment of sensitive diagnostic assays. Such assays can be based on detection of Norwalk virus nucleic acid or Norwalk vital antigen using polyclonal or monoclonal antibodies to proteins expressed from the cDNA or to synthetic peptides made based on the knowledge of the genome sequence. Vaccines made by recombinant DNA technology can also now be feasible.

1 Claim, 6 Drawing Sheets

FIG.5

```
                              21                                    41
G TGC TCT GGG AGC GGG CAT ACA GGT TGG TGG CGA CAG-GCC CTC CAA
  cys ser gly ser gly his thr gly trp trp arg gln ala leu gln 61                                    81
  AGC CAA AGG TAT CAA CAA AAT TTG CAA CTG CAA GAA AAT TCT TTT
  ser gln arg tyr gln gln asn leu gln leu gln glu asn ser phe 101                                   121
  AAA CAT GAC AGG GAA ATG ATT GGG TAT CAG GTT GAA GCT TCA AAT
  lys his asp arg glu met ile gly tyr gln val glu ala ser asn 141                              161                              181
  CAA TTA TTG GCT AAA AAT TTG GCA ACT AGA TAT TCA CTC CTC CGT
  gln leu leu ala lys asn leu ala thr arg tyr ser leu leu arg 201                                   221
  GCT GGG GGT TTG ACC AGT GCT GAT GCA GCA AGA TCT GTG GCA GGA
  ala gly gly leu thr ser ala asp ala ala arg ser val ala gly 241                                   261
  GCT CCA GTC ACC CGC ATT GTA GAT TGG AAT GGC GTG AGA GTG TCT
  ala pro val thr arg ile val asp trp asn gly val arg val ser 281                                   301
  GCT CCC GAG TCC TCT GCT ACC ACA TTG AGA TCC GGT GGC TTC ATG
  ala pro glu ser ser ala thr thr leu arg ser gly gly phe met 321                              341                              361
  TCA GTT CCC ATA CCA TTT GCC TCT AAG CAA AAA CAG GTT CAA TCA
  ser val pro ile pro phe ala ser lys gln lys gln val gln ser 381                                   401
  TCT GGT ATT AGT AAT CCA AAT TAT TCC CCT TCA TCC ATT TCT CGA
  ser gly ile ser asn pro asn tyr ser pro ser ser ile ser arg 421                                   441
  ACC ACT AGT TGG GTC GAG TCA CAA AAC TCA TCG AGA TTT GGA AAT
  thr thr ser trp val glu ser gln asn ser ser arg phe gly asn 461                                   481
  CTT TCT CCA TAC CAC GCG GAG GCT CTC AAT ACA GTG TGG TTG ACT
  leu ser pro tyr his ala glu ala leu asn thr val trp leu thr

501
```

METHODS AND REAGENTS TO DETECT AND CHARACTERIZE NORWALK AND RELATED VIRUSES This is a continuation of application Ser. No. 07/433,492, filed Nov. 8, 1989 now abandoned.

FIELD OF THE INVENTION

The present invention relates generally to synthesizing clones of Norwalk virus and to making probes to Norwalk and related viruses. It also relates to methods of detection and characterization of Norwalk and related viruses.

BACKGROUND OF THE INVENTION

Norwalk virus is one of the most important viral pathogens causing acute gastroenteritis, the second most common illness in the United States (Dingle et al., 1953; Kapikian and Chanock, 1985). Up to 65% of cases of viral gastroenteritis have been estimated to be caused by Norwalk or Norwalk-like viruses (Kaplan et al., 1982). Both water and foodborne transmission of Norwalk virus has been documented, and particularly large epidemic outbreaks of illness have occurred following consumption of contaminated shellfish including clams, cockles, and oysters (Murphy et al., 1979; Gunn et al., 1982; Wilson et al., 1982; Gill et al., 1983; DuPont 1986; Morse et al., 1986; Sekine et al., 1989). An increase in fish and shellfish-related food poisonings has recently been noted and attributed to increased recognition of these entities by clinicians as well as to increased consumption of seafood (Eastaugh and Shepherd, 1989). Norwalk virus was discovered in 1973, but knowledge about the virus has remained limited because it has failed to grow in cell culture and no suitable animal models have been found for virus cultivation. Therefore, human stool samples obtained from outbreaks and from human volunteer studies are the only source of virus. Moreover, the concentration of the virus in stool is usually so low that virus detection with routine electron microscopy is not possible (Dolin et al., 1972; Kapikian et al., 1972; Thornhill et al., 1975). Current methods of Norwalk virus detection include immune electron microscopy and other immunologic methods such as RIAs or a biotin-avidin ELISAs which utilize acute and convalescent phase serum from humans. To date, no hyperimmune serum from animals has been successfully prepared due either to insufficient quantities or unusual properties of the viral antigen. Preliminary biophysical characterization of virions has indicated particles contain 1 polypeptide (Greenberg et al., 1981), but efforts to characterize the viral genome have failed. Therefore, these viruses have remained unclassified.

LITERATURE CITED

1. Dingle J., Badger G., Feller A. et al. 1953. A study of illness in a group of Cleveland families: 1. Plan of study and certain general observations. Am. J. Hyg. 58:16–30.

2. Dolin R., Blacklow N. R., DuPont H., Buscho R. F., Wyatt R. G., Kasel J. A., Hornick R., and Chanock R. M. 1972. Biological properties of Norwalk agent of acute infectious nonbacterial gastroenteritis. Proc. Soc. Exp. Med. and Biol. 140:578–583.

3. Dolin R., Blacklow N. R., DuPont H., Formal S., Buscho R. F., Kasel J. A., Chames R. P., Hornick R., and Chanock R. M. 1971. Transmission of acute infectious nonbacterial gastroenteritis to volunteers by oral administration of stool filtrates. J. Infect. Dis. 123:307–312.

4. DuPont H L. 1986. Consumption of raw shellfish—is the risk now unacceptable? New Engl. J. Med. 314:707–708.

5. Eastaugh J, Shepherd S. 1989. Infectious and toxic syndromes from fish and shellfish consumption. Arch. Intern. Med. 149:1735–1740.

6. Gill O. N., Cubitt W. D., McSwiggan D. A., Watney B. M. and Bartlett C. L. R. 1983. Epidemic of gastroenteritis caused by oysters contaminated with small round structured viruses. Br. Med. J. 287:1532–1534.

7. Greenberg H. B., Valdesuso J. R., Kalica A. R., Wyatt R. G., McAuliffe V. J., Kapikian A. Z. and Chanock R. M. 1981. Proteins of Norwalk virus. J. Virol. 37: 994–999.

8. Gunn R. A., Janowski H. T., Lieb S., Prather E. C., and Greenberg H. B. 1982. Norwalk virus gastroenteritis following raw oyster consumption. Am. J. Epidemiol. 115:348–351.

9. Jiang X., Estes M. K., and Metcalf T. G. 1989. In situ hybridization for quantitative assay of infectious hepatitis A virus. J. Clin. Microbiol. 27:874–879.

10. Jiang X., Estes M. K., and Metcalf T. G. 1987. Detection of hepatitis A virus by hybridization with single-stranded RNA probes. Appl. Environ. Microbiol. 53:2487–2495.

11. Jiang X., Estes M. K., Metcalf T. G., and Melnick J. L. 1986. Detection of hepatitis A virus in seeded estuarine samples by hybridization with cDNA probes. Appl. Environ. Microbiol. 52:711–717.

12. Kapikian A. Z. and Chanock R. M. 1985. Norwalk group of viruses. In: BN Fields (ed.) Virology, Raven Press, New York, pp. 1495–1517.

13. Kapikian A. Z., Wyatt R. G., Dolin R., Thornhill T. S., Kalica A. R., and Chanock R. M. 1972. Visualization by immune electron microscopy of a 27-nm particle associated with acute infectious nonbacterial gastroenteritis. J. Virol. 10:1075–1081.

14. Kaplan J., Feldman R., Campbell D. et al. 1982. The frequency of a Norwalk-like pattern of illness in outbreaks of acute gastroenteritis. Am. J. Public. Health 72:1329–1332.

15. Morse D. L., Guzewich J. J., Hanrahan J. P., Stricof R., Shayegani M., Deibel R., Grabau J. C., Nowak N. A., Herrmann J. E., Cukor G., and Blacklow N. R. 1986. Widespread outbreaks of clam- and oyster-associated gastroenteritis: role of Norwalk virus. New Engl. J. Med. 314:678–681.

16. Murphy A. M., Grohmann G. S., Christopher P. J., Lopez W. A., Davey G. R, and Millsom R. H. 1979. An Australia-wide outbreak of gastroenteritis from oysters caused by Norwalk virus. Med. J. Aust. 2:329–333.

17. Sekine S., Okada S., Hayashi Y., Ando T., Terayama T, Yabuuchi K., Miki T., and Ohashi M. 1989. Prevalence of small round structured virus infections in acute gastroenteritis outbreaks in Tokyo. Microbiol. Immunol. 33:207–217.

18. Thornhill T. S., Kalica A. R., Wyatt R. G., Kapikian A. Z., and Chanock R. M. 1975. Pattern of shedding of the Norwalk particle in stools during experimentally induced gastroenteritis in volunteers as determined by immune electron microscopy. J. Infect. Dis. 132:28–34.

19. Wilson R., Anderson L. J., Holman R. C., Gary G. W., and Greenberg H. B. 1982. Waterborne gastroenteritis due to the Norwalk agent: clinical and epidemiologic investigation. Am. J. Public Health 72:72–74.

BRIEF DESCRIPTION OF THE FIGURES

FIG. 5. The nucleotide sequence of the genome sense strand of the Norwalk virus cDNA clone. The deduced amino acid sequence of a long open reading frame in this cDNA is also shown.

DETAILED DESCRIPTION OF THE INVENTION

Figure 1:
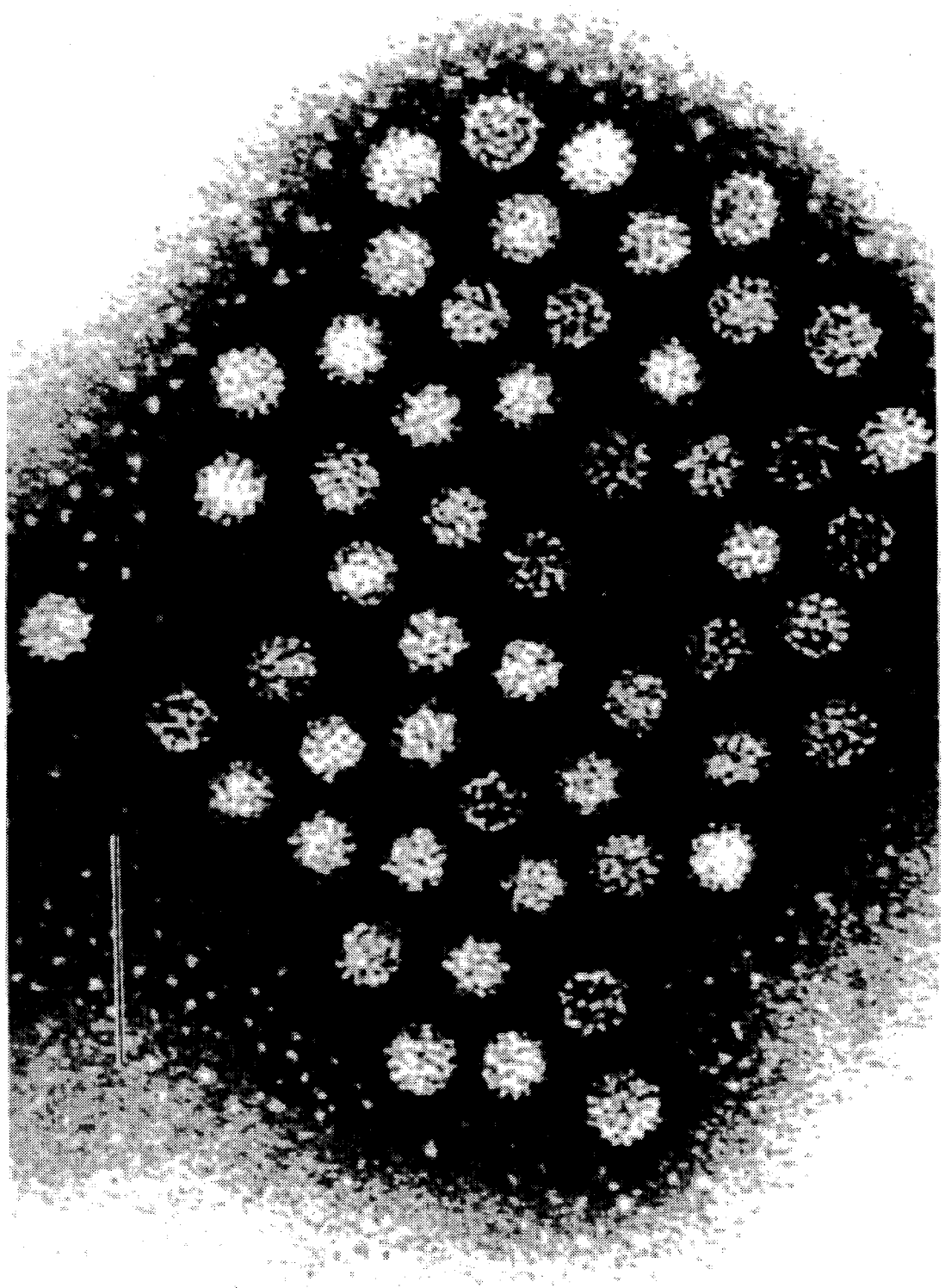
FIG. 1. EM picture of Norwalk viruses after CsCl gradient purification.

Production of Norwalk Virus for Molecular Cloning

Norwalk virus was produced by administration of safety tested Norwalk virus (8FIIa) to adult volunteers. The virus inoculum used in the volunteer study, was kindly supplied by Dr. Albert Kapikian (Laboratory of Allergy and Infectious Diseases, National Institutes of Health, Bethesda, Md.). This virus originated from an outbreak of acute gastroenteritis in Norwalk, Ohio (Dolin et al., 1971). Two ml of a 1 to 100 dilution of 8FIIa in TBS was administered orally to each individual with 80 ml of milli-Q water (Millipore, Bedford, Mass. 01730). Sodium bicarbonate solution was taken by each person 2 min before and 5 min after virus administration. The volunteer studies were approved by the Institutional Review Board for Human Research at Baylor College of Medicine, at the Methodist Hospital and at the General Clinical Research Center. The virus was administered to the volunteers in the General Clinical Research Center where the volunteers were hospitalized and under extensive medical care for 4 days. All stools were collected and kept at −70° C. for later use.

Purification of Norwalk Viruses from Stool Samples

A 10% solution of stool samples in TBS was first clarified by low speed centrifugation at 3000 rpm for 15 min. The resultant supernate was then extracted 2 to 3 times with genetron in the presence of 0.5% Zwittergent 3–14 detergent (Calbiochem Corp., La Jolla, Calif.). Viruses in the aqueous phase were concentrated by pelleting at 36,00 rpm for 90 min through a 40% sucrose cushion in a 50.2 Ti rotor (Beckman Instruments, Inc., Palo Alto, Calif. 94304). The pellets were suspended in TBS and mixed with CsCl solution (refractive index 1.368) and centrifuged at 35,000 rpm for 24 h in a SW50.1 rotor (Beckman). The CsCl gradient was fractioned by bottom puncture and each fraction was monitored for virus by EM examination. The peak fractions containing Norwalk virus were pooled and CsCl in the samples was diluted with TBS and removed by pelleting the viruses at 35,000 rpm for 1 h. The purified virus was stored at −70° C.

Extraction of Nucleic Acids from Purified Virus

Purified Norwalk virus from CsCl gradients was first treated with proteinase K (400 ug/ml) in proteinase K buffer (0.1M Tris-Cl pH 7.5, 12.5 mM EDTA, 0.15M NaCl, 1% w/v SDS) at 37° C. for 30 min. The samples were then extracted once with phenol-chloroform and once with chloroform. Nucleic acids in the aqueous phase were concentrated by precipitation with 2.5 volumes of ethanol in the presence of 0.2M NaOAc followed by pelleting for 15 min in a microcentrifuge.

cDNA Synthesis and Cloning of Amplified of cDNA

Nucleic acids extracted from the purified Norwalk viruses were denatured with 10 mM CH$_3$HgOH and cDNA was synthesized using the cDNA synthesis kit with the supplied random hexanucleotide primer (Amersham, Arlington Heights, Ill. 60005). After the second strand synthesis, the reaction mixture was extracted once with phenol-chloroform and once with chloroform followed by ethanol precipitation. Amplification of DNA was performed using the random prime kit for DNA labeling (Promega Corp., Madison, Wis. 53711–5305). Eight cycles of denaturation (100° C. for 2 min), reanealing (2 min cooling to room temperature) and elongation (room temperature for 30 min) were performed after addition of Klenow fragment (Promega Corp.). A DNA library was constructed in pUC-13 with blunt-end ligation into the Sma I site.

Screening of the Library for Positive Clones

White colonies from transformed DH5 alpha bacterial cells (BRL) were picked and both a master plate and minipreps of plasmid DNA was prepared for each clone. Clones containing inserts were identified after electrophoresis of the plasmid DNA in an agarose gel. The DNA in the agarose gel was cut out and labeled with $^{32}$P using the prime-a-gene labeling system (Promega Corp.). Nucleic acids extracted from paired stool samples (before and after Norwalk infection) from two volunteers (543 and 544) were dotted onto Zetabind filters (AFM, Cuno, Meriden, Conn.).

Replicate filter strips were prepared and hybridized with each labeled plasmid probe individually at 68° C. without formamide. Potential positive clones were judged by their different reactions with the pre- and post-infection stools. Clones which reacted with post-(but not pre-) infection stools of volunteers were considered positive and these clones on the master plates were characterized further.

To permit better diagnosis and molecular characterization of Norwalk virus, we have made a cDNA library derived from nucleic acid extracted from virions purified from stool samples. Norwalk virus was purified with methods used previously for hepatitis A and rotaviruses from stool samples with some modifications (Jiang et al., 1986). Basically stool samples obtained from volunteers administered Norwalk virus were treated with Genetron to remove lipid and water insoluble materials. Virus in the aqueous phase was then pelleted through a 40% sucrose cushion. The resultant pellets were resuspended, sonicated and loaded in a CsCl gradient for isopycnic centrifugation. FIG. 1 shows an electron micrograph of purified Norwalk viruses after CsCl gradient centrifugation. Approximately $10^9$ physical particles were obtained from 500 grams of stools.

A cDNA library was generated from nucleic acids extracted from these purified viruses by proteinase K treatment of the samples followed by phenol-chloroform extraction and ethanol precipitation (Jiang et al., 1986; 1987). Because the nature of the viral genome was unknown, the extracted nucleic acids were denatured with methylmercuric hydroxide before cDNA synthesis. Random primed cDNA was synthesized with the Gubler-Hoffman method (cDNA synthesis system plus, Amersham) and a small amount of cDNA was obtained. Direct cloning of this small amount of cDNA was unsuccessful. Therefore, a step of amplification of the DNA was performed by synthesizing more copies of the DNA with random primers and the Klenow fragment of DNA polymerase before cloning. The procedure involved 35 cycles of denaturation, addition of random primers and the Klenow fragment of DNA polymerase, reannealing and elongation. With this procedure, a linear incorporation of labeled nucleotides into product was observed as the number of cycles of synthesis was increased. The numbers of cycles performed were limited (<10) to avoid the synthesis of an excess of smaller fragments. In the case of Norwalk cDNA, 8 cycles of amplification were performed and approximately 2.5 ug of DNA were obtained, which was at least a 100-fold amplification of the starting template cDNA. This amplified cDNA was cloned into pUC-13 by blunt end ligation and a positive clone (pUCNV-953) was isolated.

Figure 2A:
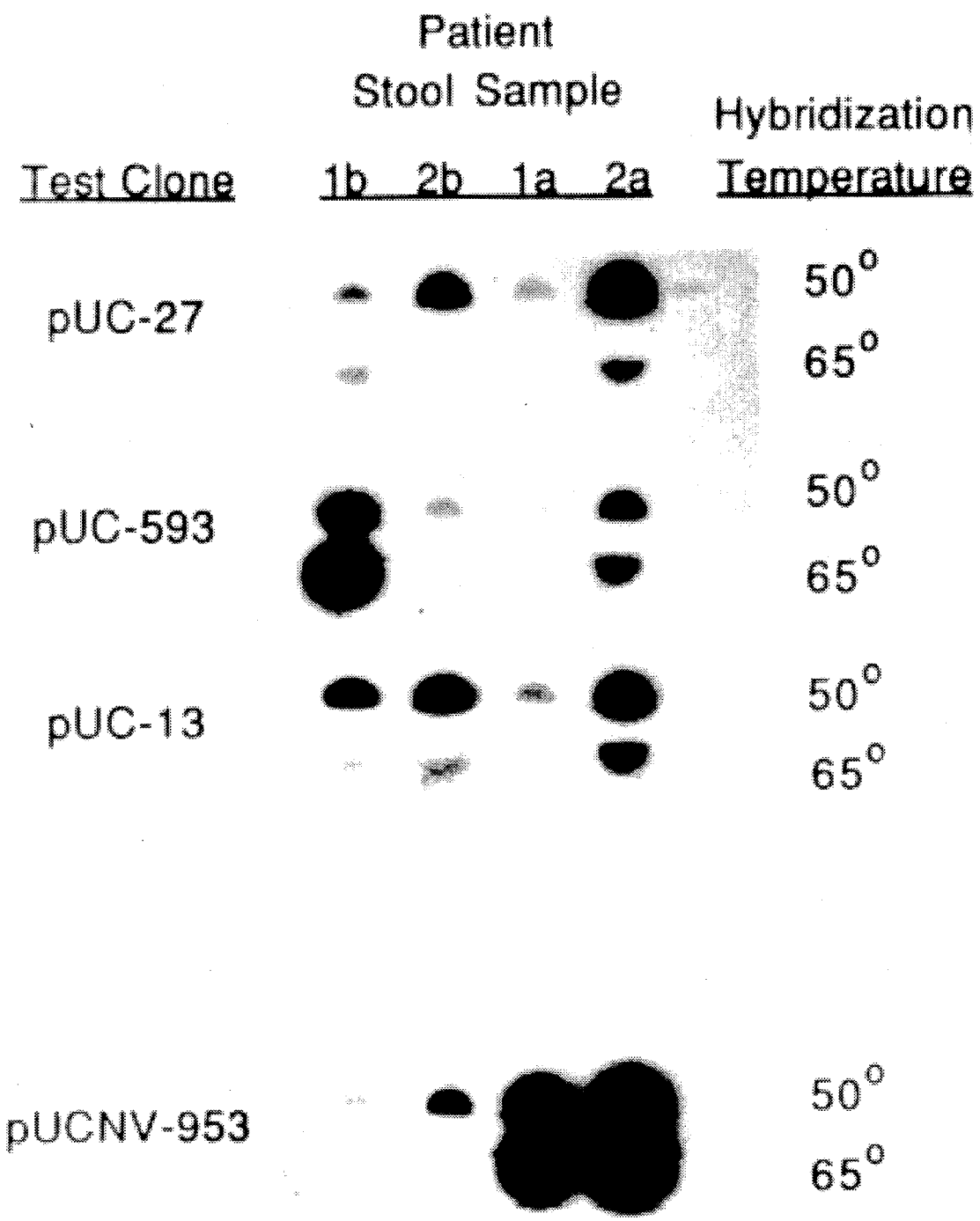
FIG. 2a Hybridization of stool samples with $^{32}$P labeled plasmid DNA for screening positive Norwalk cDNA clones. Nucleic acids from paired stools [before (b) and after (a) infection with Norwalk virus] from two volunteers (1 and 2) were dotted on Zetabind filters. Replicate strips were prepared and hybridized at 50° C. and 65° C. with each test clone (pUC-27, pUC-593, pUC-13 and pUC-953). One clone (pUCNV-953) which reacted only with stool samples after (but not before) Norwalk infection was considered as a potential positive clone and was chosen for further characterization.

To obtain the positive Norwalk virus clone, minipreparations of the plasmid DNAs containing potential inserts were screened by agarose gel electrophoresis. The larger clones in the gel were cut out and probes were made with the DNA in the gel using the prime-a-gene labeling system (Promega Corp.). These probes were hybridized individually with paired stool samples (before and after Norwalk infection) from two volunteers (FIG. 2a). One clone (pUCNV-953) reacted with post- but not pre-infection stool samples from both volunteers.

Figure 2B:
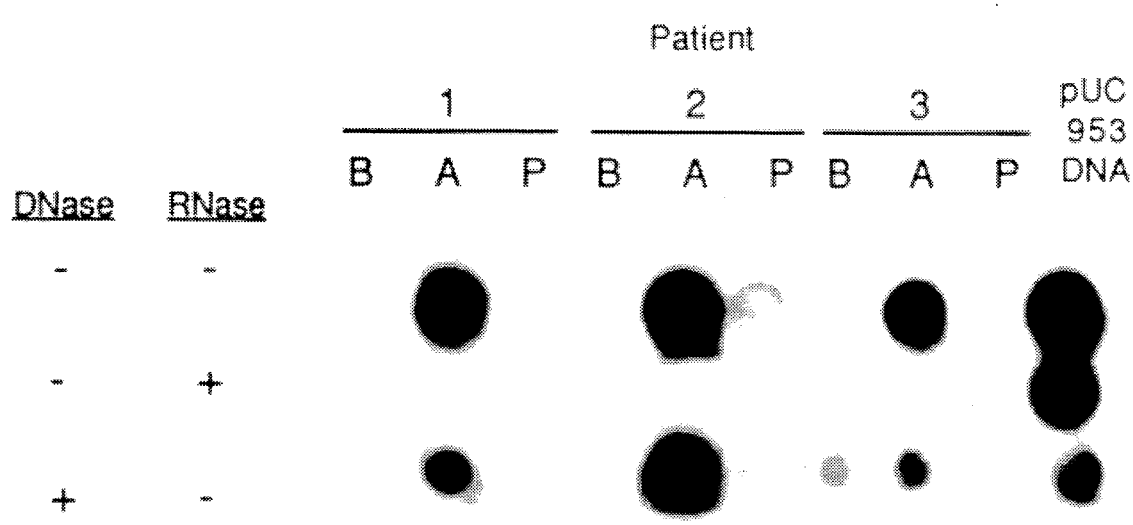
FIG. 2b. Dot blot hybridization of clone pUCNV-953 with another 3 sets of stool samples collected at different times after infection (B=before acute phase of illness; A=acute phase of illness; P=post-acute phase of illness) of 3 volunteers. The nucleic acids were dotted directly or after treatment with RNAse or with DNAse before dotting. Double stranded homologous cDNA (pUCNV-953) was dotted after the same treatments as the stool samples.
Figure 3:
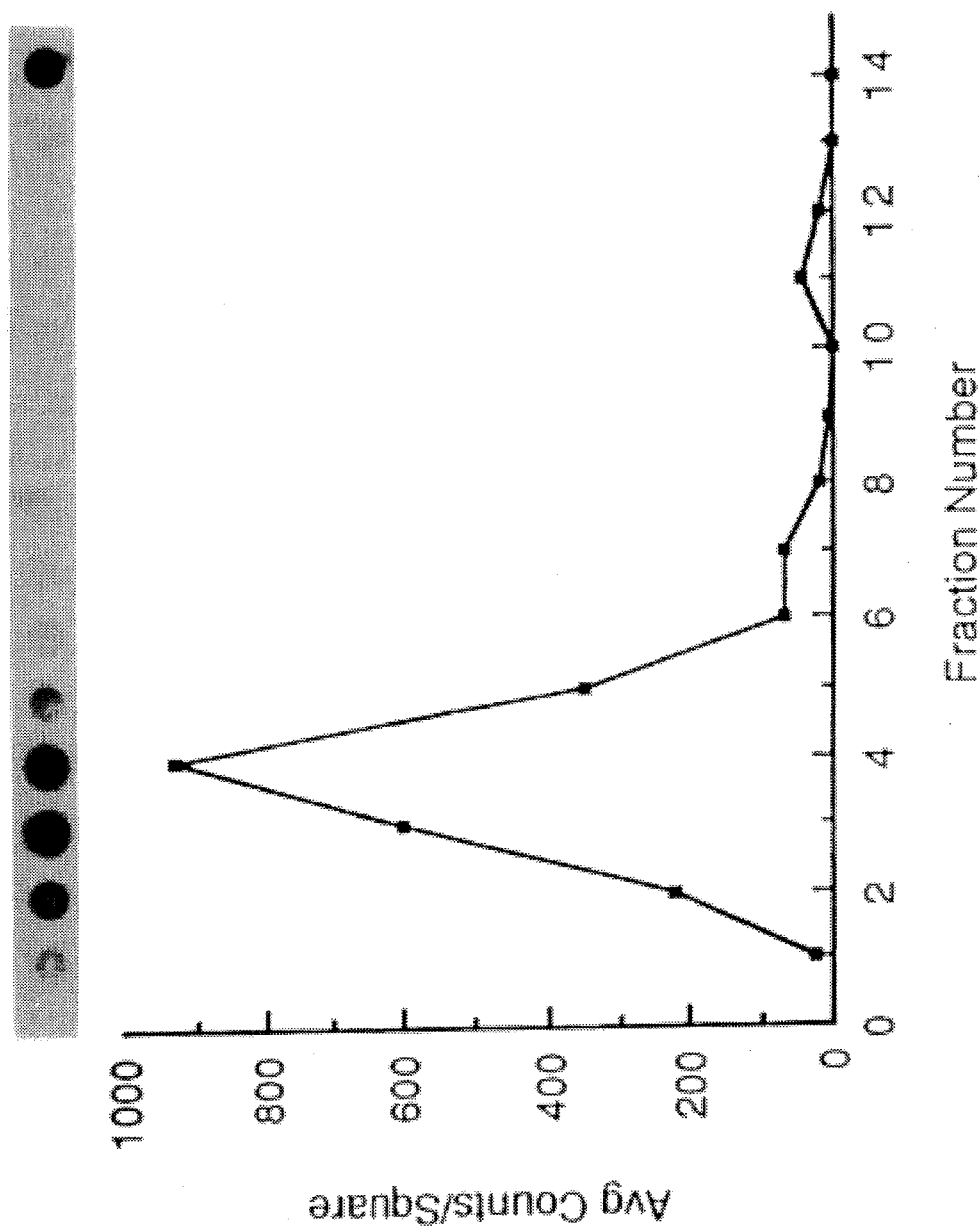
FIG. 3. Dot blot hybridization of Norwalk viruses in a CsCl gradient with ssRNA probes made from pGEMNV-953. Aliquots of 50 ul from each fraction in a CsCl gradient were dotted onto a Zetabind filter. Duplicates of filters were made and hybridized with the two ssRNA probes respectively. The two strands were subsequently called cRNA (positive hybridization with the vital nucleic acid) and vRNA (no hybridization with the viral nucleic acid). Graph shows EM counts of Norwalk viruses from each fraction of the same CsCl gradient for the dot blot hybridization. Five squares from each grid were counted and the average of the number of vital particles per square was calculated.
Figure 4:
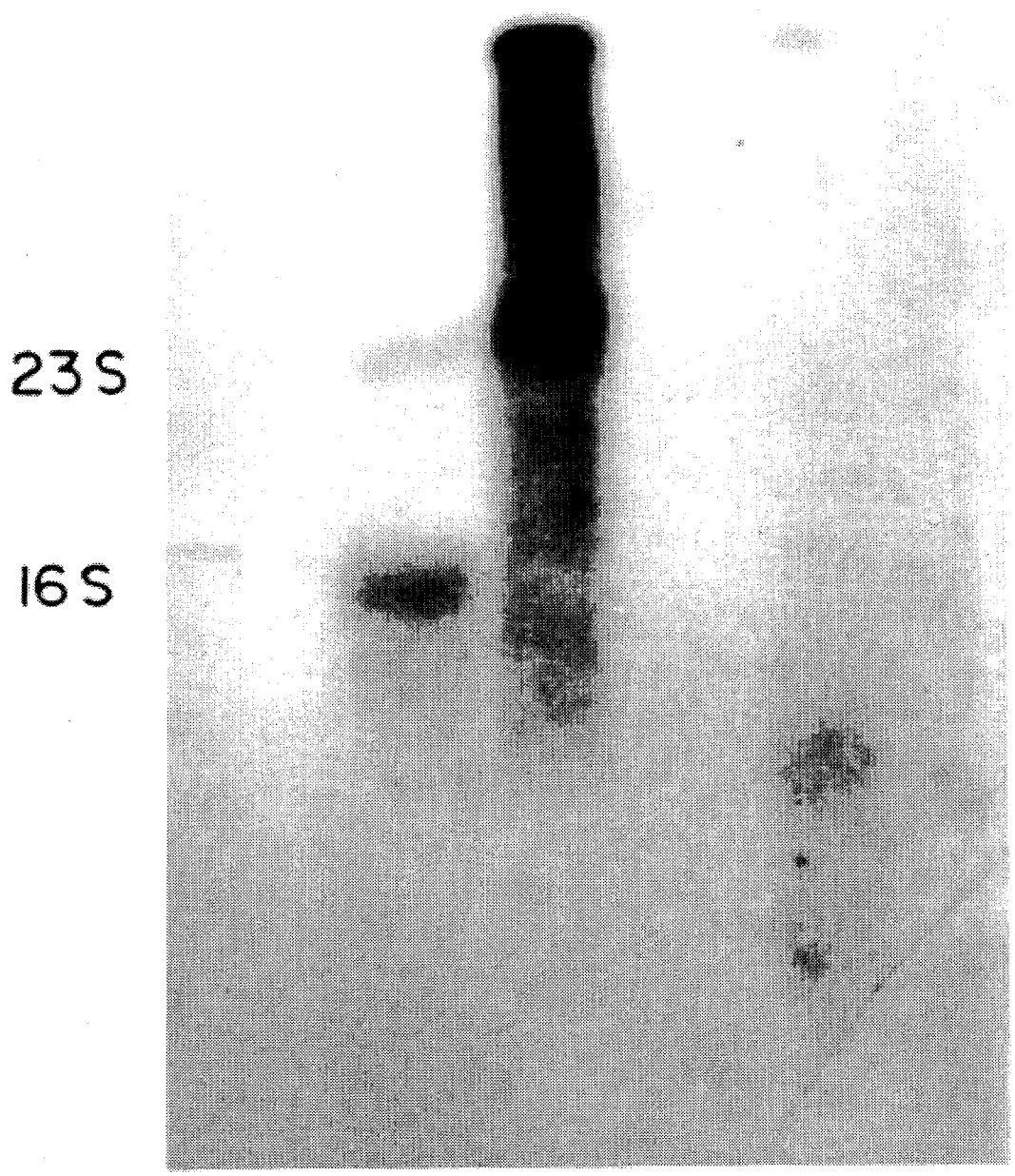
FIG. 4. Hybridization of Norwalk viral RNA with clone pUCNV-953. Nucleic acids extracted from partially purified viruses were electrophoresed in a native agarose gel as described previously (Jiang et al., 1989). The gel was then dried at 80° C. for 1 h and hybridized with $^{32}$P labeled pUCNV-953 insert. Lane 1, 23 S and 16 S rRNA from E. coli (Miles Laboratories Inc., Naperville, Ill. 60566), lanes 2 and 4, total nucleic acids from partially purified stool samples containing Norwalk virus, and lane 3, HAV RNA.

To further confirm the vital origin of the clone pUCNV-953, 6 more paired stool samples were tested and the same results were obtained. FIG. 2b shows a dot blot hybridization of the clone with stool samples collected at different times post-infection of the disease. Strong signals were observed only with stools from acute phase, but not before and after the illness. This result was consistent with previous RIA assays for viral antigen detection using convalescent sera from volunteers with Norwalk diarrhea and immune electron microscopy (IEM) studies of the samples for viral particle examination. This result also agrees with the patterns of virus shedding in stool in the course of the disease (Thornhill et al., 1975). When the clone was hybridized with fractions of a CsCl gradient from the Norwalk virus purification scheme, a correlation between hybridization and EM vital particle counts was observed (FIG. 3). The peaks of the hybridization signals and viral particle counts both were at fractions with a density of 1.38 g/cm$^3$ which agrees with 9revious reports of the biophysical properties of Norwalk virus. Finally, the clone was tested by hybridization with highly purified Norwalk virus electrophoresed on an agarose gel. A single hybridization band was observed with Norwalk virus but not with HAV and rotavirus (FIG. 4). Sequence analysis of the pUCNV-953 cDNA showed this clone is 511 bp (FIG. 5); this partial genomic cDNA encodes a potential open reading frame (FIG. 5). No significant nucleotide or deduced amino acid sequence homology was found by comparison with other sequences in the Gen Bank (Molecular Biology Information Resource, Eugene Software, Baylot College of Medicine).

We also used this first Norwalk virus cDNA to begin to characterize the viral genome. The pUCNV-953 cDNA was subcloned into the transcription vector pGEM-3Zf(+) and ssRNA probes were generated by in vitro transcription using SP6 and T7 polymerases (Promega). When two opposite sense ssRNA probes were hybridized with the vital nucleic acid separately, only one strand reacted with the virus, indicating the viral genome is single stranded. As shown in FIG. 2b, the hybridization signals were removed by treatment of the viral nucleic acid with RNAse (but not with DNAse) before loading them onto the filters, indicating the virus genome contains ssRNA. A long open reading frame was found in one of the two strands of the inserted DNA by the computer analysis of the sequences of pUCNV-953. The ssRNA probe with the same sequence as this coding strand did not react with the vital nucleic acid, but the complementary ssRNA probe did react in the hybridization tests. Therefore, Norwalk virus contains a positive stranded RNA genome. The size of the genome of Norwalk virus was estimated to be about 8 kb based on comparisons of the migration rate of the purified vital RNA in agarose gels with molecular weight markers. This size is slightly bigger than that of the picornaviruses [HAV and poliovirus; (FIG. 4)].

This cDNA or fragments thereof can be used in assays to detect the genome of Norwalk and other related viruses. The detection assays can include labeled cDNA or ssRNA probes for direct detection of the Norwalk virus genome. Alternatively, small oligonucleotide probes and polymerase chain reaction amplification can also be used to detect the Norwalk and related virus genomes. Expression of the open reading frame in the cDNA can be used to make hyperimmune or monoclonal antibodies for use in diagnostic products and vaccines.

What is claimed is:

1. A method of synthesizing a clone of Norwalk virus, comprising the steps of:

isolating single stranded RNA from a Norwalk virus;

synthesizing a cDNA with reverse transcriptase and random primers;

synthesizing a second strand DNA from said cDNA;

amplifying said second strand DNA;

inserting at least one copy of said second strand DNA into a plasmid;

and screening said plasmid to identify clones containing fragments of the Norwalk virus genome.

* * * * *